United States Patent [19]

Bettinger et al.

[11] 4,014,651

[45] Mar. 29, 1977

[54] METHOD FOR DETERMINING THYROID FUNCTION AND REAGENT COMPOSITION THEREFOR

[75] Inventors: Ella M. Bettinger, St. Louis, Mo.; Everett K. Mincey, Vancouver, Canada

[73] Assignee: Mallinckrodt, Inc., St. Louis, Mo.

[22] Filed: May 15, 1975

[21] Appl. No.: 577,859

Related U.S. Application Data

[63] Continuation-in-part of Ser. No. 360,660, May 14, 1973, abandoned.

[52] U.S. Cl. .................................. 23/230.6; 424/1.5
[51] Int. Cl.$^2$ ........................................ G01N 33/16
[58] Field of Search ...................... 23/230 B, 230.6; 424/111, 357, 1, 1.5; 252/408

[56] References Cited

UNITED STATES PATENTS

| | | | |
|---|---|---|---|
| 3,507,618 | 4/1970 | Murty et al. | 23/230 B |
| 3,519,390 | 7/1970 | Dickey et al. | 23/230 B |
| 3,666,854 | 5/1972 | Eisentraut | 23/230 B UX |
| 3,672,845 | 6/1972 | Verbeck | 23/253 TP |
| 3,816,262 | 6/1974 | Monte et al. | 252/408 X |

*Primary Examiner*—Morris O. Wolk
*Assistant Examiner*—Arnold Turk
*Attorney, Agent, or Firm*—Koenig, Senniger, Powers and Leavitt

[57] ABSTRACT

A complete and self-contained in vitro diagnostic reagent composition for use in determining thyroid function comprises a buffered aqueous suspension of finely divided, amorphous silicon dioxide, having combined therewith a nonionic surfactant and a thyroid hormone substance tagged or labeled with radioisotopic iodine.

6 Claims, No Drawings

METHOD FOR DETERMINING THYROID FUNCTION AND REAGENT COMPOSITION THEREFOR

CROSS-REFERENCE TO RELATED APPLICATION

This application is a continuation-in-part of application Ser. No. 360,660 and now abandoned, filed May 14, 1973.

BACKGROUND OF THE INVENTION

1. Field of the Invention

The present invention relates to the field of clinical diagnostic reagents and more particularly to reagents containing a hormone substance tagged with radioisotopic iodine and useful for in vitro (thyroid) function determinations.

2. Description of the Prior Art

It is known to measure the unsaturated binding capacity of blood serum by admixing a sample of serum with a buffered solution containing a known amount of thyroid hormone labeled with a radioactive isotope of iodine and an ion-exchange resin or other solid sorbent substance such as charcoal, talc, magnesium silicate, and the like capable of binding the excess labeled hormone so that it can be separated and removed from the serum sample. The amount of labeled hormone taken up by the serum protein, primarily thyroxine-binding globulin, can then be determined directly or indirectly using a scintillation counter. Such tests are commonly known in the art as T-3 tests.

In the most commonly used forms of this test, the solid sorbent material is added after the serum sample and the labeled hormone solution are combined in which case the function of the sorbent is limited to binding the excess, i.e. free or unbound, hormone so that it can be separated from the liquid serum sample containing the protein-bound hormone.

In another form of this test (U.S. Pat. No. 3,507,618), the labeled hormone is initially bound to an ion-exchange resin, and in this form the test depends upon desorption of the hormone from the ion-exchange resin carrier. This method is satisfactory provided that the charged resin is freshly prepared and is kept thoroughly dry up until the moment of actual use, and provided that all times and temperatures are carefully standardized and precisely controlled.

A major defect with this method is that with time, and especially in the presence of moisture, the labeled hormone becomes permanently bound to the resin and therefore unavailable for binding by the blood serum protein. The combination of a labeled hormone and an exchange resin is therefore entirely unsuitable for use in a complete and self-contained liquid reagent composition that can be prepared and stored for future use.

Eisentraut U.S. Pat. No. 3,666,854 discloses a method for determining thyroid function in which particulate inorganic crystalline materials are employed as sorbent materials, and specifically disclcoses the use of silicic acid and opal, for example. However, we have found that amorphous silicon dioxide per se is not particularly effective when employed as the sorbent material in a test for determining thyroid function.

SUMMARY OF THE INVENTION

Among the objects of the present invention may be noted the provision of novel radioactive diagnostic reagent compositions for the in vitro determination of thyroid function; the provision of compositions of the character described in the form of an aqueous suspension which contains therein all the essential reagent substances for measuring the unsaturated thyroxine binding capacity of blood serum protein; the provision of compositions of the character described which may be packaged and stored in units of a size just sufficient for testing a single sample of blood serum; the provision of such compositions which remain usable for the effective life of the radioactive isotope contained therein; and the provision of methods for using the aforesaid compositions. Other objects and features of the invention will be in part apparent and in part pointed out hereinafter.

The present invention is thus directed to a diagnostic reagent composition for use in measuring the unsaturated thyroid hormone binding capacity of blood serum. The reagent comprises a buffered aqueous suspension of finely divided, amorphous silicon dioxide which additionally contains a nonionic surfactant and a thyroid hormone substance such as thyroxine tagged or labeled with a radioactive isotope of iodine, the weight to weight ratio of amorphous silica to nonionic surfactant in the suspension being in the range of approximately 10:1 to 50:1. The invention also includes the method of using such a reagent composition in the in vitro determination of thyroid function.

DESCRIPTION OF THE PREFERRED EMBODIMENTS

In carrying out the method of the present invention, a measured amount of the blood serum to be tested is mixed with the novel reagent composition of the invention, the amorphous silicon dioxide is separated from the liquid portion of the sample, e.g. by centrifugation, after which the radioactivity of either the solid silicon dioxide residue or the supernatant liquid is determined using a conventional scintillation well counter.

The method is based upon desorption of the labeled hormone from the silicon dioxide carrier by certain proteins, notably thyroxine-binding globulin, in the blood serum. Unlike desorption methods employed in the past, the present method is essentially independent of time and temperature and the reagent composition of the invention is complete and self-contained.

In the novel diagnostic reagent composition of the present invention, the radioactive isotope labeled hormone is releasably bound to the amorphous silicon dioxide which together with the nonionic surfactant serves as a solid carrier. Thus, when serum is mixed with the reagent, the unsaturated binding sites present in the thyroxine-binding globulin of the serum take labeled hormone from the carrier until the binding capacity is substantially saturated. The excess labeled hormone remains bound to the silicon dioxide carrier. This transfer occurs practically instantaneously at ordinary room temperatures, and therefore the method is essentially independent of time and temperature. As soon as convenient, the solid silicon dioxide containing the excess labeled hormone is separated from the liquid portion of the sample which contains the protein bound hormone, i.e. the substantially saturated thyroxine-binding globulin. This is easily and quickly accomplished by centrifugation. Since the total amount of labeled hormone initially present in the reagent composition is known or easily determined, the amount of such hormone taken up by the serum protein can be determined by counting either the supernatant liquid or the separated solid silicon dioxide using a conventional scintillation counter.

Numerous nonionic surfactants suitable for use in the present invention are disclosed in *Kirk-Othmer Encyclopedia of Chemical Technology*, Second Edition, Volume 19, pages 531–554. Among those which have been found particularly suitable may be noted polyoxyethylene alcohols, polyoxyethylene sorbitan fatty acid esters, nonylphenoxypoly (ethyleneoxy) ethanol and sorbitan fatty acid esters.

The reagent composition of the present invention is in the form of a buffered aqueous suspension which may be packaged and stored in units just sufficient for a single test and the container in which the method of the invention is carried out may be a test vial of the kind and size customarily used with a conventional scintillation counter.

The labeled hormone may be either L-thyroxine (T-4) or L-triiodothyronine (T-3) tagged or labeled with a radioactive isotope of iodine such as I-125 or I-131. Such hormones are well known and are used in most if not all in vitro methods for measuring thyroid function.

In accordance with the present invention, it has more specifically been found that the employment in the reagent composition of amorphous silicon dioxide, and nonionic surfactant in a (w/w) ratio of approximately 10:1 to 50:1 provides particularly good results as compared to the use of amorphous silicon dioxide alone as the sorbent material.

The following examples illustrate the invention.

EXAMPLE 1

A suspension of 20 g. of microfine precipitated silica ("QUSO G-32" manufactured by Philadelphia Quartz Co.) was suspended in 2000 ml. of a pH 7.3 ($\pm 0.1$) buffer solution having the following composition:

| | | |
|---|---|---|
| Tris(hydroxymethyl)aminomethane | | 48.4 g. |
| HCl | | 29.8 ml. |
| Water | to make | 2 liters |

To this suspension was added an aqueous solution containing 1.0 g. of nonylphenoxypoly (ethyleneoxy) ethanol ("Igepal CO-880" manufactured by Applied Science Laboratories, Inc.). The suspension was thoroughly mixed and then sufficient T-3 labeled with I-131 was added to give between 50,000 – 100,000 cpm/3 ml. in a conventional scintillation counter. The suspension was then dispensed into glass vials, 3.0 ml./vial.

EXAMPLE 2

The reagent vials described in Example 1 are used in the following manner in determining the thyroxine-binding capacity of blood serum protein:

1. Add 0.1 ml. of patient serum to a reaction vial. Also add 0.1 ml. of control serum in a reaction vial.
2. Mix all of the vials by inverting several times or place on a vortex mixer for 10 seconds.
3. Allow the vials to stand for 5 minutes at room temperature.
4. Centrifuge the vials for 5 minutes at 2500 rpm or until the adsorbent is packed.
5. Decant the supernatant fluid, which is discarded, and drain the tubes for 1 minute on a paper towel.
6. Count the vials of patient serum and control serum and calculate the index.

$$\text{Index} = \frac{\text{Net patient cpm}}{\text{Net control cpm}}$$

EXAMPLE 3

Example 1 was repeated except that polyoxyethylene (20) oleyl ether sold under the trade designation "BRIJ 98" by Atlas Chemical Industries, Inc. was used as the nonionic surfactant.

EXAMPLE 4

Example 1 was repeated except that polyoxyethylene (20) sorbitan monolaurate sold under the trade designation "Tween 20" by Atlas Chemical Industries, Inc. was used as the nonionic surfactant.

EXAMPLE 5

Example 1 was repeated except that sorbitan monolaurate sold under the trade designation "Span 20" by Atlas Chemical Industries, Inc. was used as the nonionic surfactant.

The compositions and method described in Examples 1–5 were applied to a wide range of serum samples and the results compared favorably in precision and accuracy with the results obtained using other more time-consuming methods known heretofore.

EXAMPLE 6

The following tests were carried out to determine the comparative results between carrying out the thyroid function determination above described with and without the incorporation of a nonionic surfactant in the diagnostic reagent composition.

The procedure of Example 1 was followed in preparing 100 ml. each of suspensions containing 0.5, 1.0, 3.0 and 5.0% of microfine precipitated silica ("QUSO G-32" manufactured by Philadelphia Quartz Co.) and no nonionic surfactant and in preparing 100 ml. each of suspensions containing the same silica and the nonionic surfactant nonylphenoxypoly (ethyleneoxy) ethanol ("Igepal CO-880" manufactured by Applied Science Laboratories, Inc.) in the weight by weight ratios of 1:1, 5:1, 10:1, 20:1, 30:1, 40:1, 50:1 and 100:1. The buffer solution of Example 1 was used in preparing these suspensions. The resulting suspensions contained the quantities of labeled triiodothyronine (T3) as described in Example 1. All of the suspensions prepared were dispensed into glass vials, 3.0 ml./vial.

Reaction vials labeled B for "Button" or blank to which no serum was added, were shaken, precounted and placed on a vortex mixer for 10 seconds. They were then spun for 5 minutes at 2500 rpm or until the adsorbent was packed, the supernatant decanted, and the vials drained for a minute on a paper towel before being postcounted. After the addition of 0.1 ml. of serum, the sample vials were mixed, allowed to stand for 2 minutes before being placed on a vortex mixer for about 10 seconds, spun at 2500 rpm for 5 minutes or until the adsorbent was packed, the supernatant decanted and the vials drained for a minute on a paper towel before being postcounted, all as described in Example 2. The percent uptake of labeled triiodothyronine (T3) was calculated by dividing the postcount in cpm by the precount in cpm. The sera used for these tests were MONI-TROL I (normal or euthyroid) and MONI-TROL II (hyperthyroid) synthetic control sera available commercially from Dade Division of American Hospital Supply Corporation. For these tests, the same vials of reconstituted controls were used.

The results are as follows:

| % Silica Conc. | mg. Silica/ml. Dispersion | % Uptake B | I | II | Δ%, I – II |
|---|---|---|---|---|---|
| 0.5 | 5 | 6.0 | 15.4 | 19.1 | 3.7 |
| 1 | 10 | 13.6 | 23.1 | 26.2 | 3.1 |
| 3 | 30 | 28.8 | 42.4 | 43.5 | 1.1 |
| 5 | 50 | 42.9 | 56.8 | 56.1 | −0.7 |

| Ratio Silica: Nonionic Surfactant (w/w) | mg. Silica: mg. nonionic Surfactant/ml. Dispersion | % Uptake B | I | II | Δ%, I – II |
|---|---|---|---|---|---|
| 1:1 | 10:10 | 25.9 | 25.0 | 26.6 | 1.6 |
| 5:1 | 10:2.0 | 90.3 | 74.5 | 79.1 | 4.6 |
| 10:1 | 10:1.0 | 89.0 | 58.2 | 71.3 | 13.1 |
| 20:1 | 10:0.5 | 82.0 | 44.3 | 55.3 | 11.0 |
| 30:1 | 10:0.333 | 78.0 | 36.4 | 50.0 | 13.6 |
| 40:1 | 10:0.25 | 74.0 | 33.2 | 43.5 | 10.3 |
| 50:1 | 10:0.2 | 69.7 | 33.1 | 44.5 | 11.4 |
| 100:1 | 10:0.1 | 48.0 | 28.9 | 34.1 | 5.2 |

With respect to the values reported for B in the first tests with silica only as the sorbent, it is probable that agents normally present in the blood serum which have surfactant characteristics are interacting with the silica to cause higher uptake as to the MONI-TROL I and II sera samples.

The above data indicate rather clearly that the incorporation of the nonionic surfactant in the formulation increases the Δ % or difference in % uptakes between the two MONI-TROL control values. Without an appreciable increase in the differential between the % uptake by these two controls, accurate test results differentiating between normal thyroid function and hyperthyroid or hypothyroid function cannot be achieved.

In view of the above, it will be seen that the several objects of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A diagnostic reagent composition for use in the in vitro determination of thyroid function comprising a buffered aqueous suspension containing:
    a. finely divided, amorphous silicon dioxide;
    b. a thyroid hormone substance tagged with radioactive iodine; and
    c. a nonionic surfactant;
the weight to weight ratio of said amorphous silica to said nonionic surfactant being in the range of approximately 10:1 to 50:1.

2. A diagnostic reagent composition as set forth in claim 1 wherein said thyroid hormone substance is selected from the group consisting of L-thyroxine and L-triiodothyronine.

3. A diagnostic reagent composition as set forth in claim 1 wherein said nonionic surfactant is selected from the group consisting of polyoxyethylene alcohols, polyoxyethylene sorbitan fatty acid esters, nonylphenoxypoly (ethyleneoxy) ethanols and sorbitan fatty acid esters.

4. The method for the in vitro determination of thyroid function which comprises the steps of
mixing a blood serum sample with a measured amount of a reagent composition comprising a buffered aqueous suspension containing
    a. finely divided amorphous silicon dioxide;
    b. a thyroid hormone substance tagged with radioactive iodine; and
    c. a nonionic surfactant;
the weight to weight ratio of said amorphous silica to said nonionic surfactant being in the range of approximately 10:1 to 50:1;
separating the silicon dioxide from the resulting suspension; and
measuring the radioactivity of the separated silicon dioxide residue or the supernatant liquid.

5. The method as set forth in claim 4 wherein said thyroid hormone substance is selected from the group consisting of L-thyroxine and L-triiodothyronine.

6. The method as set forth in claim 4 wherein said nonionic surfactant is selected from the group consisting of polyoxyethylene alcohols, polyoxyethylene sorbitan fatty acid esters, nonylphenoxypoly (ethyleneoxy) ethanols and sorbitan fatty acid esters.

* * * * *